United States Patent [19]
Bova

[11] Patent Number: 6,080,428
[45] Date of Patent: *Jun. 27, 2000

[54] NICOTINIC ACID COMPOSITIONS FOR TREATING HYPERLIPIDEMIA AND RELATED METHODS THEREFOR

[76] Inventor: David J. Bova, 1201 S. Ocean Dr., Apt. 8085, Hollywood, Fla. 33019

[*] Notice: This patent is subject to a terminal disclaimer.

[21] Appl. No.: 08/368,378

[22] Filed: Jan. 14, 1995

Related U.S. Application Data

[63] Continuation-in-part of application No. 08/124,392, Sep. 20, 1993, abandoned.

[51] Int. Cl.$^7$ ...................................................... A61K 9/22
[52] U.S. Cl. ........................... 424/468; 424/464; 424/469; 424/470
[58] Field of Search ................................... 424/464, 468, 424/469, 470

[56] References Cited

U.S. PATENT DOCUMENTS

| | | |
|---|---|---|
| 29,652 | 5/1860 | Fields et al. . |
| 32,581 | 1/1888 | Scherm et al. . |
| 2,510,164 | 6/1950 | Woodward et al. . |
| 2,540,979 | 2/1951 | Clymer et al. . |
| 2,749,274 | 6/1956 | Buckwalter . |
| 2,798,837 | 7/1957 | Sahyun . |
| 2,798,838 | 7/1957 | Robinson . |
| 2,805,977 | 9/1957 | Robinson et al. . |
| 2,851,453 | 9/1958 | Kennon et al. . |
| 2,857,313 | 10/1958 | Cooper et al. . |
| 2,887,436 | 5/1959 | Klioze et al. . |
| 2,957,804 | 10/1960 | Schuyler . |
| 3,062,720 | 11/1962 | Costello . |
| 3,108,046 | 10/1963 | Harbit . |
| 3,116,204 | 12/1963 | Siegel et al. . |
| 3,134,719 | 5/1964 | Sheth et al. . |
| 3,143,469 | 8/1964 | Debay et al. . |
| 3,147,187 | 9/1964 | Playfair . |
| 3,193,461 | 7/1965 | Elsen . |
| 3,210,413 | 10/1965 | Blank et al. . |
| 3,272,832 | 9/1966 | Nakano et al. . |
| 3,336,200 | 8/1967 | Krause et al. . |
| 3,424,842 | 1/1969 | Nurnberg . |
| 3,495,011 | 2/1970 | Fossel . |
| 3,590,117 | 6/1971 | Christenson et al. . |
| 3,626,071 | 12/1971 | Kariya et al. . |
| 3,629,393 | 12/1971 | Nakamoto et al. . |
| 3,629,453 | 12/1971 | Waring . |
| 3,634,584 | 1/1972 | Poole . |
| 3,639,636 | 2/1972 | Barnhart . |
| 3,709,991 | 1/1973 | Miller . |
| 3,721,735 | 3/1973 | Thiffault . |
| 3,773,920 | 11/1973 | Nakamoto et al. . |
| 3,795,691 | 3/1974 | Douglas et al. . |
| 3,806,601 | 4/1974 | Mikite et al. . |
| 3,849,554 | 11/1974 | Winitz . |
| 3,859,437 | 1/1975 | Weigand . |
| 3,862,332 | 1/1975 | Barnhart et al. . |
| 3,868,416 | 2/1975 | Albright et al. . |
| 3,870,790 | 3/1975 | Lowey et al. . |
| 3,923,972 | 12/1975 | Fields et al. . |
| 3,924,001 | 12/1975 | Albright et al. . |
| 3,930,017 | 12/1975 | Kummer et al. . |
| 3,951,821 | 4/1976 | Davidson . |
| 3,957,976 | 5/1976 | Sugimoto . |
| 3,959,492 | 5/1976 | Coulston et al. . |
| 3,965,255 | 6/1976 | Bloch et al. . |
| 3,977,404 | 8/1976 | Theeuwes . |
| 3,987,160 | 10/1976 | Broughton et al. . |
| 3,992,536 | 11/1976 | Kleemann et al. . |
| 4,002,641 | 1/1977 | Moller et al. . |
| 4,008,719 | 2/1977 | Theeuwes et al. . |
| 4,011,339 | 3/1977 | Galantay et al. . |
| 4,014,334 | 3/1977 | Theeuwes et al. . |
| 4,014,987 | 3/1977 | Heller et al. . |
| 4,034,087 | 7/1977 | Voorhees . |
| 4,034,758 | 7/1977 | Theeuwes . |

(List continued on next page.)

FOREIGN PATENT DOCUMENTS

| | | |
|---|---|---|
| 603690 | 8/1960 | Canada . |
| 0109320 | 5/1984 | European Pat. Off. . |
| 0126453 | 11/1984 | European Pat. Off. . |
| 0 109 320 B1 | 6/1986 | European Pat. Off. . |
| 0109320 | 6/1986 | European Pat. Off. . |
| 0 349 236 A3 | 1/1990 | European Pat. Off. . |
| 0 577 504 A1 | 1/1990 | European Pat. Off. . |
| 1302362 | 7/1962 | France . |
| 40-2053 | 2/1965 | Japan . |
| 46-18151 | 5/1971 | Japan . |
| 0049312 | 4/1980 | Japan . |
| 2141338 | 12/1984 | United Kingdom . |
| 2154874 | 9/1985 | United Kingdom . |
| 8400104 | 1/1984 | WIPO . |

OTHER PUBLICATIONS

"Circadian variation in the frequency of sudden cardiac death" by Muller et al., *Pathophysiology and Natural History*, vol. 75, No. 1, Jan. 1987, p. 1 only, (1 page).

"Contrasting Effects of Unmodified and Time–Release Forms of Niacin on Lipoproteins in Hyperlipidemic–Subjects: Clues to Mechanism of Action of Niacin" by Knopp et al., *Metabolism*, vol. 34, No. 7, pp. 642–650, Jul. 1985.

"Diurnal Patterns of Triglycerides, Free Fatty Acids, Blood Sugar, and Insulin during Carbohydrate–Induction in Man and Their Modification by Nocturnal Suppression of Lipolysis" by Schlierf et al., *The Journal of Clinical Investigation*, vol. 52, pp. 732–740, Mar. 1973.

(List continued on next page.)

*Primary Examiner*—Jyothsna Venkat

[57] ABSTRACT

An orally administered antihyperlipidemia composition according to the present invention includes from about 250 to about 3000 parts by weight of nicotinic acid, and from about 5 to about 50 parts by weight of hydroxypropyl methylcellulose. Also, a method of treating hyperlipidemia in a hyperlipidemic having a substantially periodic physiological loss of consciousness, includes the steps of forming a composition having an effective antihyperlipidemic amount of nicotinic acid and a time release sustaining amount of a swelling agent. The method also includes the step of orally administering the composition to the hyperlipidemic once per day "nocturnally", that is in the evening or at night.

13 Claims, No Drawings

U.S. PATENT DOCUMENTS

| | | |
|---|---|---|
| 4,058,122 | 11/1977 | Theeuwes et al. . |
| 4,067,876 | 1/1978 | Ferruti et al. . |
| 4,077,407 | 3/1978 | Theeuwes et al. . |
| 4,102,806 | 7/1978 | Kondo et al. . |
| 4,115,550 | 9/1978 | Fields et al. . |
| 4,116,241 | 9/1978 | Theeuwes et al. . |
| 4,117,111 | 9/1978 | Fields et al. . |
| 4,126,672 | 11/1978 | Sheth et al. . |
| 4,140,755 | 2/1979 | Sheth et al. . |
| 4,160,020 | 7/1979 | Ayer et al. . |
| 4,160,452 | 7/1979 | Theeuwes . |
| 4,166,902 | 9/1979 | Ferruti et al. . |
| 4,167,558 | 9/1979 | Sheth et al. . |
| 4,169,944 | 10/1979 | Scallen et al. . |
| 4,178,387 | 12/1979 | Diamond et al. . |
| 4,180,064 | 12/1979 | Heller et al. . |
| 4,182,902 | 1/1980 | Thiele et al. . |
| 4,203,439 | 5/1980 | Theeuwes . |
| 4,205,085 | 5/1980 | Shepherd . |
| 4,211,783 | 7/1980 | Shepherd . |
| 4,226,849 | 10/1980 | Schor . |
| 4,230,878 | 10/1980 | Shepherd . |
| 4,237,118 | 12/1980 | Howard . |
| 4,248,857 | 2/1981 | DeNeale et al. . |
| 4,251,519 | 2/1981 | Robbins et al. . |
| 4,255,449 | 3/1981 | Cavazza . |
| 4,256,108 | 3/1981 | Theeuwes . |
| 4,259,314 | 3/1981 | Lowey ............................................ 424/19 |
| 4,261,970 | 4/1981 | Ogawa et al. . |
| 4,268,524 | 5/1981 | Cavazza . |
| 4,272,548 | 6/1981 | Gatzen et al. . |
| 4,279,898 | 7/1981 | Engel et al. . |
| 4,282,233 | 8/1981 | Vilani . |
| 4,283,382 | 8/1981 | Frank et al. . |
| 4,285,951 | 8/1981 | Hoefle . |
| 4,291,030 | 9/1981 | Mulinos . |
| 4,305,959 | 12/1981 | Shepherd . |
| 4,308,251 | 12/1981 | Dunn et al. . |
| 4,309,404 | 1/1982 | DeNeale et al. . |
| 4,310,545 | 1/1982 | Shepherd . |
| 4,318,914 | 3/1982 | Shepherd . |
| 4,326,525 | 4/1982 | Swanson et al. . |
| 4,348,399 | 9/1982 | Shepherd . |
| 4,353,887 | 10/1982 | Hess et al. . |
| 4,357,469 | 11/1982 | Schor . |
| 4,361,546 | 11/1982 | Stricker et al. . |
| 4,362,711 | 12/1982 | Cerami . |
| 4,367,217 | 1/1983 | Gruber et al. . |
| 4,369,172 | 1/1983 | Schor et al. ................................ 424/19 |
| 4,375,468 | 3/1983 | Dunn . |
| 4,382,143 | 5/1983 | Shepherd . |
| 4,389,393 | 6/1983 | Schor et al. ................................ 424/19 |
| 4,428,951 | 1/1984 | Hata et al. . |
| 4,432,966 | 2/1984 | Zeitoun et al. ............................ 424/21 |
| 4,440,940 | 4/1984 | Shepherd . |
| 4,452,775 | 6/1984 | Kent . |
| 4,454,108 | 6/1984 | Iida et al. . |
| 4,455,298 | 6/1984 | McFarlane et al. . |
| 4,457,907 | 7/1984 | Porter . |
| 4,461,759 | 7/1984 | Dunn . |
| 4,465,660 | 8/1984 | David et al. . |
| 4,472,436 | 9/1984 | Hooper . |
| 4,478,819 | 10/1984 | Hercelin et al. . |
| 4,485,105 | 11/1984 | Shepherd . |
| 4,522,804 | 6/1985 | Dunn . |
| 4,525,345 | 6/1985 | Dunn et al. . |
| 4,539,198 | 9/1985 | Powell et al. . |
| 4,540,566 | 9/1985 | Davis et al. . |
| 4,547,359 | 10/1985 | Zierenberg et al. . |
| 4,556,678 | 12/1985 | Hsiao . |
| 4,568,547 | 2/1986 | Herschler . |
| 4,571,333 | 2/1986 | Hsiao et al. . |
| 4,576,604 | 3/1986 | Guittard et al. . |
| 4,603,142 | 7/1986 | Burger et al. . |
| 4,605,666 | 8/1986 | Schmidt et al. . |
| 4,610,870 | 9/1986 | Jain et al. . |
| 4,624,950 | 11/1986 | Sasaki et al. . |
| 4,657,757 | 4/1987 | Hanna et al. . |
| 4,673,405 | 6/1987 | Guittard et al. . |
| 4,678,516 | 7/1987 | Alderman et al. . |
| 4,680,323 | 7/1987 | Lowey . |
| 4,684,516 | 8/1987 | Bhutani . |
| 4,690,824 | 9/1987 | Powell et al. . |
| 4,692,337 | 9/1987 | Ukigaya et al. . |
| 4,695,467 | 9/1987 | Uemura et al. . |
| 4,695,591 | 9/1987 | Hanna et al. . |
| 4,695,910 | 9/1987 | Maruyama et al. . |
| 4,696,762 | 9/1987 | Sander et al. . |
| 4,704,285 | 11/1987 | Alderman . |
| 4,708,834 | 11/1987 | Cohen et al. . |
| 4,710,519 | 12/1987 | Finnan et al. . |
| 4,713,245 | 12/1987 | Ando et al. . |
| 4,729,895 | 3/1988 | Makino et al. . |
| 4,734,285 | 3/1988 | Alderman . |
| 4,747,881 | 5/1988 | Shaw et al. . |
| 4,749,575 | 6/1988 | Rotman . |
| 4,752,479 | 6/1988 | Briggs et al. .......................... 424/472 |
| 4,753,801 | 6/1988 | Oren et al. . |
| 4,755,544 | 7/1988 | Makino et al. . |
| 4,756,911 | 7/1988 | Drost et al. . |
| 4,758,581 | 7/1988 | Scherm et al. . |
| 4,759,923 | 7/1988 | Buntin et al. . |
| 4,764,374 | 8/1988 | Grimberg . |
| 4,775,483 | 10/1988 | Mookerjea et al. . |
| 4,775,535 | 10/1988 | Lowey . |
| 4,777,042 | 10/1988 | Toda et al. . |
| 4,784,858 | 11/1988 | Ventouras . |
| 4,789,549 | 12/1988 | Kahn et al. . |
| 4,792,452 | 12/1988 | Howard et al. . |
| 4,792,554 | 12/1988 | Elben et al. . |
| 4,794,115 | 12/1988 | Takahashi et al. . |
| 4,795,327 | 1/1989 | Gaylord et al. . |
| 4,795,642 | 1/1989 | Cohen et al. .......................... 424/455 |
| 4,795,644 | 1/1989 | Zentner . |
| 4,803,079 | 2/1989 | Hsiao et al. . |
| 4,803,081 | 2/1989 | Falk et al. . |
| 4,812,316 | 3/1989 | Rossi et al. . |
| 4,814,183 | 3/1989 | Zentner . |
| 4,814,354 | 3/1989 | Ghebre-Sellassie et al. . |
| 4,824,672 | 4/1989 | Day et a. . |
| 4,824,677 | 4/1989 | Shah et al. . |
| 4,828,836 | 5/1989 | Elger et al. . |
| 4,830,859 | 5/1989 | Finnan et al. . |
| 4,834,965 | 5/1989 | Martani et al. . |
| 4,834,985 | 5/1989 | Elger et al. . |
| 4,837,032 | 6/1989 | Ortega . |
| 4,839,177 | 6/1989 | Colombo et al. . |
| 4,842,863 | 6/1989 | Nishimura et al. . |
| 4,844,907 | 7/1989 | Elger et al. . |
| 4,849,229 | 7/1989 | Gaylord et al. . |
| 4,851,232 | 7/1989 | Urquhart et al. . |
| 4,851,233 | 7/1989 | Khan et al. . |
| 4,855,143 | 8/1989 | Lowey . |
| 4,857,336 | 8/1989 | Khanna et al. . |
| 4,866,058 | 9/1989 | Izydore et al. . |
| 4,871,548 | 10/1989 | Edgren et al. . |
| 4,882,167 | 11/1989 | Jang . |
| 4,886,669 | 12/1989 | Ventouras . |
| 4,888,178 | 12/1989 | Rotini et al. . |
| 4,892,741 | 1/1990 | Ohm et al. . |
| 4,911,917 | 3/1990 | Kuhrts . |
| 4,915,952 | 4/1990 | Ayer et al. . |

| | | |
|---|---|---|
| 4,920,115 | 4/1990 | Nestler et al. . |
| 4,920,123 | 4/1990 | Beyer, Jr. . |
| 4,925,905 | 5/1990 | Boeckh et al. . |
| 4,935,246 | 6/1990 | Ahrens . |
| 4,940,588 | 7/1990 | Sparks et al. . |
| 4,942,040 | 7/1990 | Ragnarsson et al. . |
| 4,946,870 | 8/1990 | Partain, III et al. . |
| 4,946,963 | 8/1990 | Izydore et al. . |
| 4,950,689 | 8/1990 | Yang et al. ............................. 514/777 |
| 4,952,402 | 8/1990 | Sparks et al. . |
| 4,959,478 | 9/1990 | Moller et al. . |
| 4,963,367 | 10/1990 | Ecanow . |
| 4,965,252 | 10/1990 | Kuhrts . |
| 4,966,768 | 10/1990 | Michelucci et al. . |
| 4,970,081 | 11/1990 | Frisbee . |
| 4,973,468 | 11/1990 | Chiang et al. .......................... 424/449 |
| 4,973,469 | 11/1990 | Mulligan et al. . |
| 4,983,398 | 1/1991 | Gaylord et al. . |
| 4,990,535 | 2/1991 | Cho et al. . |
| 4,992,278 | 2/1991 | Khanna . |
| 4,994,267 | 2/1991 | Seblotsky ................................ 424/78 |
| 4,994,276 | 2/1991 | Baichwal et al. . |
| 4,996,058 | 2/1991 | Sinnreich . |
| 4,997,658 | 3/1991 | Alberts et al. . |
| 4,999,380 | 3/1991 | Berger et al. . |
| 5,009,895 | 4/1991 | Lui . |
| 5,010,105 | 4/1991 | Lee ......................................... 514/510 |
| 5,011,947 | 4/1991 | Catt et al. ............................... 549/292 |
| 5,015,479 | 5/1991 | Mulligan et al. . |
| 5,022,774 | 6/1991 | Kageyama et al. . |
| 5,023,245 | 6/1991 | Kuhrts . |
| 5,025,012 | 6/1991 | Miura et al. . |
| 5,030,653 | 7/1991 | Trivedi ................................... 514/510 |
| 5,032,406 | 7/1991 | Dansereau et al. . |
| 5,034,528 | 7/1991 | Izydore et al. . |
| 5,039,341 | 8/1991 | Meyer . |
| 5,047,248 | 9/1991 | Calanchi et al. . |
| 5,049,696 | 9/1991 | Lee et al. ................................. 560/75 |
| 5,096,714 | 3/1992 | Kuhrts . |
| 5,100,675 | 3/1992 | Cho et al. . |
| 5,110,817 | 5/1992 | Beyer, Jr. . |
| 5,110,940 | 5/1992 | Sit et al. ................................. 548/252 |
| 5,116,610 | 5/1992 | Broaddus ............................. 424/78.12 |
| 5,126,145 | 6/1992 | Evenstad et al. . |
| 5,128,142 | 7/1992 | Mulligan et al. . |
| 5,130,333 | 7/1992 | Pan et al. . |
| 5,132,116 | 7/1992 | Sournac et al. . |
| 5,133,974 | 7/1992 | Paradissis et al. . |
| 5,145,678 | 9/1992 | Gakic et al. . |
| 5,167,964 | 12/1992 | Mohammed et al. . |
| 5,169,638 | 12/1992 | Dennis et al. . |
| 5,169,639 | 12/1992 | Baichwal et al. . |
| 5,169,640 | 12/1992 | France et al. . |
| 5,171,570 | 12/1992 | Takemori et al. . |
| 5,178,854 | 1/1993 | Asami et al. . |
| 5,182,298 | 1/1993 | Helms et al. . |
| 5,188,839 | 2/1993 | Pearmain . |
| 5,190,940 | 3/1993 | Commons et al. . |
| 5,190,970 | 3/1993 | Pan et al. . |
| 5,196,440 | 3/1993 | Bertolini et al. . |
| 5,211,958 | 5/1993 | Akkerboom et al. . |
| 5,213,808 | 5/1993 | Bar-Shalom et al. . |
| 5,256,689 | 10/1993 | Chiang . |
| 5,258,401 | 11/1993 | Berger et al. . |
| 5,260,305 | 11/1993 | Dennick . |
| 5,262,165 | 11/1993 | Govil et al. . |
| 5,262,435 | 11/1993 | Joshua et al. . |
| 5,264,226 | 11/1993 | Graille et al. . |
| 5,268,181 | 12/1993 | O'Neill et al. .......................... 424/465 |
| 5,278,067 | 1/1994 | Dawson et al. . |
| 5,286,736 | 2/1994 | Soyka et al. . |
| 5,314,697 | 5/1994 | Kwan et al. . |

OTHER PUBLICATIONS

"Diurnal Variation of Tissue–Type Plasminogen Activator and Its Rapid Inhibitor (PAI–1)" by Angleton et al., from the Department of Laboratory Medicine, Univ. of Washington, Sep. 1988 (1 page).

"Hepatotoxicity Associated with Sustained–Release Niacin" by Dalton et al., *The American Journal of Medicine*, vol. 93, pp. 102–104, Jul. 1992.

"Impaired Fibrinolytic Capacity and Tissue Plasminogen Activator Release in Patients with Restenosis after Percutaneous Transluminal Coronary Angioplasty (PTCA)" by Kirchstein et al., *Thrombosis and Haemostasis*, 1989, p. 1 only (1 page).

"Increased Plasma Levels of a Rapid Inhibitor of Tissue Plasminogen Activator in Young Survivors of Myocardial Infarction" by Hamsten et al., *The New England Journal of Medicine*, vol. 313, No. 25, pp. 1557–1563, Dec. 19, 1985.

"Inhibition of Carbohydrate–Induced Hypertriglyceridemia by Nicotinic Acid" by Schlierf et al., *Artery*, vol. 3(2), pp. 174–179 (1977).

"Major Circadian Fluctuations in Fibrinolytic Factors and Possible Relevance to Time of Onset of Myocardial Infarction, Sudden Cardiac Death and Stroke" by Andreotti et al., *The American Journal of Cardiology*, p. 635, Sep. 15, 1988.

"Niacin–Induced Hepatitis: A Potential Side Effect with Low–Dose Time–Release Niacin" by Etchason et al., *Mayo Clin Proc*, vol. 66, pp. 23–28, 1991.

"Niacin Revisted: Clinical Observations on an Important but Underutilized Drug" by Henkin et al., *The American Journal of Medicine*, vol. 91, pp. 239–246, Sep. 1991.

"Plasminogen Activator Inhibitors" by Sprengers et al., *Blood*, vol. 69, No. 2, pp. 381–387, Feb. 1987.

"Biphasic Nature of Blood Glucose and Free Fatty Acid Changes Following Intravenous Nicotinic Acid in Man" *Preliminary Communications*, vol. 27, pp. 440–443, Mar. 1967.

"The Pathogenesis of Atherosclerosis—An Update" by Ross, *The New England Journal of Medicine*, vol. 314, No. 8, pp. 488–500, Feb. 20, 1986.

"The role of the fibrinolytic system in deep vein thrombosis" by Ljungberg et al., from departments of Karolinska Hospital (1 page) Oct. 1984.

"Insulin, Cortisol and Catecholamines Do Not Regulate Circadian Variations in Fibrinolytic Activity" by Chandler et al., *Thrombosis Research* vol. 58, No. 1, pp. 1–12, 1990.

1 page Derwent Abstract of Japanese Patent No. JP63310827 A 881219 DW8905 (translated).

1 page Derwent Abstract of Japanese Patent No. JP5221854 A 930831 DW9339 A61K9/22 010pp (translated).

Lexis Database copy of U.S. Pat. No. RE 32,581, Jan. 19, 1988, (Level 1) pp. 2–11.

Lexis Database copy of U.S. Pat. No. 5,032,608, Jul. 16, 1991, (Level 1) pp. 12–37.

Lexis Database copy of U.S. Pat. No. 5,032,608, Jul. 16, 1991, (Level 2) pp. 13–38.

Lexis Database copy of U.S. Pat. No. 5,023,245, Jun. 11, 1991, (Level 1) pp. 38–58.

Lexis Database copy of U.S. Pat. No. 4,758,581, Jul. 19, 1988, (Level 2) pp. 39–47.

Lexis Database copy of U.S. Pat. No. 4,911,917, Mar. 27, 1990, (Level 1) pp. 72–80.

Lexis Database copy of U.S. Pat. No. 4,758,581, Jul. 19, 1988, (Level 1) pp. 81–89.

Lexis Database copy of U.S. Pat. No. 4,661,353, Apr. 28, 1987, (Level 2) pp. 48–62.
Hunninghake (ed.), "Clinical Experience With Niacin," in Issues in Cholesterol Management: Reappraisal of Niacin, Upsher–Smith Laboratories, Inc. (publisher) (1990).
Kruse W et al: *Eur J Clin Pharmacol* 16:11–15(1979).
Altschul R: *Arch Biochem Biophys*, 54:448–559(1995).
Carlson L A et al: *Acta med. Scand.* 183:457–465(1968).
Neuvonen P J et al: *Br J olin Pharmac.* 32:473–476(1991).
Keenan J M et al: *Jags*, 40:12–18(1992).
Cayen M N et al: *Arterioschlorisis* 45(3):281–290(Dec., 1982).
Subissi A et al: *J. Pharm. Pharmacol.* 35(9)571–575(Sep., 1983).
Criscuoli M et al: *Arterioscholerosis* 53(1):59–68(1984).
Renzetti A R et al: *J. Pharm Pharmacol.* 37(12):906–909(Dec.,1985).
Miettinen T A: *Annals of Clinical Research* 12:295–298(1980).
Miettinen T A: *Metabolism* 34(5):425–430(May, 1985).
Miettinen T A: *J. Lipid Research*, 23:466–473(1982).
*JAMA*:264(2):181(Jul. 11, 1990).
Schlierf G et al: *Artery* 3(2):174–179(1977).
Schlierf G et al: *J. Clin. Invest.* 52(3):732–740(Mar., 1973).
Schlierf G et al: *PharmacologicalControl of Lipid Metabolism, Proceedings of the Fourth InternationalSymposium on Drugs Affecting Lipid Metabolism, Philadelphia, PA,* 26:319–320(Sep., 1971).
Hunnunghake D B: Upsher–Smith Laboratories,Inc. publications(1990).
Slow Niacin Advertisement, *American Druggist*, 141–142 (Apr., 1988).
Regulatory Letter to Upsher–Smith Laboratories, Jun. 6, 1988.
Formulating for Controlled Release with Methocel cellulose Ethers, 1989 Dow Chemical Company Publications. p. 4.
Jacobson T A et al: *The American Journal of Cardiology*, 73:25D–29D (May 26, 1994).
Squires R W et al: *Mayo Clin. Proc.*, 67:855–860 (1992).
Rader J I et al: *The American Journal of Medicine*, 92:77–81 (Jan., 1992).
Keenan J M: JAMA Specialty Journal Abstracts 266(16):2209 (1991)
Keenan J M et al: Arch. Intern. Med., 151:1424–1432 (Jul. 1991).
Henkin Y et al: JAMA, 264(2):241–243 (1990).
Handbook of Nonprescription Drugs, Nutritional Supplements, 9th Edition, American Pharmaceutical Association, 470–471 (1990).
Schulman K A et al: JAMA, 264(23):3025–3033 (Dec. 19, 1990).
Brown G et al: The New England Journal of Medicine 323(19):1289–1298 (Nov. 8, 1990).
Alderman J D et al: Am. J. Cardiol., 64(12):725–729 (Oct. 1, 1989).
Carlson L A et al: J. Internal Medicine, 226–271–76 (1989).
Blum C B et al: JAMA, 261(24):3582–3587 (1989).
1989 Dow Chemical.
Kowalski R E: The 8–Week Cholesterol Cure, Harper & Row, Publishers, 95–115.
Manninen M et al: JAMA, 260(5):641–651 (1988).
Figge H L et al: J. Clin. Pharmacol, 28:1136–1140 (1988).
Figge H L et al: Pharmacotherapy, 8(5):287–294 (1988).
Urburg M et al: The Journal of Family Practice, 27(6):603–606 (1988).
Wahlberg G et al: Acta. Med. Scand., 224:319–327 (1988).
Chain Drug Review Publication, p. 12, Jun. 6, 1988, P. Leiner.
Cooper K H: Bantan Books, Dr. Kenneth H. Cooper's Preventive Medicine Program, Controlling Cholesterol, 244–253 (1988).
Urberg M et al: Metabolism, 36(9):896–899 (Sep., 1987).
Blankenham D H et al: JAMA, 257(23):159–166 (Jun. 19, 1987).
Canner P L et al: JACC, 8(6):1245–1255 (Dec., 1986).
This space intentionally left blank.
This space intentionally left blank.
Sokoloski T D: Solutions and Phase Equilibila, in Remington's 17th Edition Pharmaceutical Sciences, Mack Publishing Company, 207–208 (1985).
Dow Chemical Company publication, 1–15 (1985).
The Merck Index, Merck & Co. Inc., Tenth Edition, 809, 520,351,466 (1983).
Korsmeyer R W et al: *Journal of Pharmaceutical Sciences*, 72(10):1189,1191 (Oct. 1983).
Malkowska S et al: *Drug Development and Industrial Pharmacy*, Marcel Dekker, Inc., 9(3):349–361 (1983).
Davis S S et al: *Modern Concepts in Nitrate Delivery Systems*, 29–37, edited by A.A.J. Goldberg and D.G. Parsons, 1983: Royal Society of Medicine Int'l. Congress & Symposium Series No. 54, published jointly by Academic Press Inc. (London) Ltd., and Royal Society of Medicine.
Kane J P et al: *The New England Journal of Medicine*, 304(5):251–258 (Jan. 29, 1981).
Chowhan Z T et al: *Journal of Pharmaceutical Sciences*, 70(1):1134–1139 (Oct., 1981).
Cayen M N: *Drug Metabolism Reviews*, 11(2):291–323 (1980).
Rowland M et al: *Clinical Pharmacokinetics: Concepts and Applications* publication, Les & Febiger, 111 (1980).
Chowhan Z T: *Journal of Pharmaceutical Sciences*, 69(1):1–3 (Jan., 1980).
Gudsoorkar, V R et al: *Indian Drugs & Pharmaceuticals Industry*, 3–4 (Jul.–Aug., 1980).
Ibrahim, S A et al: *Pharmazie*, 35(8):567 (1980).
Pintye–Hodi K et al: *Pharmazier*, 35(3):168–170 (1980).
Buriet P et al: *Pharm. ACTA Helv.*, 33(7–8):189–197 (1980).
Shepherd J et al: *J. Clin. Invest.* 63:858–867 (May, 1979).
Salomon J L et al: *Pharm. ACTA Helv.*, 54(3):82–85 (1979).
Salomon J L et al: *Pharm. ACTA Helv.*, 54(3):75–85 (1979).
Salomon J L et al: *Pharm. Ind.*, 41(8):799–802 (1979).
Abumrad N A et al: *Journal of Lipid Research*, 19:423–432 (1978).
Chowhan T et al: *Journal of Pharmaceutical Sciences*, 67(10):1385–1389 (Oct., 1978).
Kereaztes N A et al: *Pharmazie*, 33(1):747–749 (1978).
The Coronary Project Research Group: *JAMA*, 231(4):36–381 (Jan. 27, 1975).
Laguna O et al: *Annales Pharmaceutiques Francaises*, 33(5):235–242 (1975).
Fleischman A I et al: *Fed. Proc.* 34(1), 248 (1975).
*Remington's Pharmaceutical Sciences*, 1576–1587 (1975).
*Remington's Pharmaceutical Sciences*, 1242–1251 (1975).
Schlierf G et al: *Nutr. Metabol.*, 13:80–91 (1971).
Barter P J et al: *The Journal of Clinical Investigation*, 50:583–591 (1971).
Miettinen T A: *Annals of Clinical Research*, 2:300–320 (1970).
Ekstrom–Jodal B et al: *Pharmacologia Clinica*, 2:86–89 (1970).

Lapidus H et al: *Journal of Pharmaceutical Sciences*, 57(8):1292–1301 (Aug. 1968).

Carlson L A et al: *Acta Med Scand*, 183(5):457–465 (May 1968).

Lapidus H et al: *Journal of Pharmaceutical Sciences*, 57(8):1292–1301 (Aug. 1968).

Carlson L A et al: *The Journal of Clinical Investigation*, 47:1795–1805 (1968).

Carlson L A et al: *Progr. Biochem. Pharmacol.*, 3:151–166 (1967).

Pinter E.J. et al: *Preliminary Communictations*, 27:440–443 (Mar. 1967).

Lapidus H: *University Microfilms International*, Thesis, Rutgers University, 1–117 (1983).

Lapidus H et al: *Journal of Pharmaceutical Sciences*, 55(8):840–843 (Aug. 1966).

Huber H E et al: *Journal of Pharmaceutical Sciences*, 55:974–976 (Sep. 1966).

Carlson L A: *Clinica Crimica Acta*, 13:349–350 (1966).

Carlson L A et al: *Acta Medica Scandinavica*, 179:453–461 (fasc. 4, 1966).

Altschul R et al: *Charles C. Thomas*, 42–135 (1964).

Mahl M: *The American Journal of the Medical Sciences*, 64:673–677 (Dec., 1963).

Carlson L A: *Acta Medica Scandinavica*, 173:719–722 (fasc. 6, 1963).

Carlson L A et al: *Acta Medica Scandinavica*, 172:641–645 (fasc. 6, 1962).

Berge K G et al: *American Journal of Medicine*, 31:24–35 (Jul. 1961).

Christensen N A et al: *J.A.M.A.*, 177(8):76–80 (Aug. 26, 1961).

Altschul R et al: *Academic Press Inc.*, 51:308–309 (1954).

Miller O N et al: *American Journal of Clinical Nutrition*, 8:480–490 (Jul.–Aug. 1960).

Carlson L A: *Annals New York Academy of Sciences*, III(471):118–143.

Dow Chemical.

Kassem A A et al: *Department of Pharmaceuticals, Faculty of Pharmacy, Cairo University*, 275–306.

Lapidus H: *Chemistry*, 2363–B–2364–B (1967).

Dow Chemical: *Handbook on Methocel\* Cellulose Ether Products*.

Svedmyr N: *Clinical Pharmacology and Therapeutics*, 559–570.

Alderman J D et al: *Clinical Research*, Abstract 1883, III–471 (Oct. 1985).

Carlson, L A: *Annals New York Academy of Sciences*, 119–142 (19).

Dow Chemical: (19).

Kassem A A et al: *Jami et Al–Qahira, Faculty of Pharmacy, Bulletin, Cairo*, 19(1):275–306 (1980).

Lapidus H: *Chemistry, Abstract*, (order No. 67–14, 728) 2363–B2364–B (1967).

Dow Chemical Company Publication: (1974).

Svedmyr N et al: *Clinical Pharmacology and Therapeutics*, 10(4):559–570 (19).

NICOTINIC ACID COMPOSITIONS FOR TREATING HYPERLIPIDEMIA AND RELATED METHODS THEREFOR

RELATED PATENT APPLICATIONS

This application is a Continuation-In-Part of abandoned U.S. patent application Ser. No. 08/124,392 filed Sep. 20, 1993.

TECHNICAL FIELD

This invention generally relates to compositions of nicotinic acid useful for treating hyperlipidemia and methods of treating hyperlipidemia employing such compositions. More particularly, the present invention employs a composition of nicotinic acid, derivatives and mixtures thereof, and a swelling agent to form a time release sustaining composition for nocturnal or evening dosing. Specifically, the present invention employs a composition of nicotinic acid and hydroxypropyl methylcellulose to treat hyperlipidemia in a once per day oral dosage form given during the evening hours.

BACKGROUND OF THE INVENTION

Nicotinic acid has been used for many years in the treatment of hyperlipidemia. This compound has long been known to exhibit the beneficial effects of reducing total cholesterol, low density lipoproteins or "LDL cholesterol", triglycerides and apolipoprotein a (Lp(a)) in the human body, while increasing desirable high density lipoproteins or "HDL cholesterol".

Nicotinic acid has normally been administered three times per day after meals. This dosing regimen is known to provide a very beneficial effect on blood lipids as discussed in Knopp et al; "Contrasting Effects of Unmodified and Time-Release Forms of Niacin on Lipoproteins in Hyperlipidemic Subjects: Clues to Mechanism of Action of Niacin"; Metabolism 34/7, 1985, page 647. The chief advantage of this profile is the ability of nicotinic acid to decrease total cholesterol, LDL cholesterol, triglycerides and Lp (a) while increasing HDL particles. While such a regimen does produce beneficial effects, cutaneous flushing and the like still often occurs in the hyperlipidemics to whom the compound is administered.

In order to avoid or reduce the cutaneous flushing a number of materials have been suggested for administration with an effective antihyperlipidemic amount of nicotinic acid, including guar gum in U.S. Pat. No. 4,965,252, and mineral salts as disclosed in U.S. Pat. No. 5,023,245; or inorganic magnesium salts as reported in U.S. Pat. No. 4,911,917. These materials have been shown to the cutaneous flushing of the side effects commonly associated with nicotinic acid treatment.

Another method of avoiding or reducing the side effects associated with immediate release niacin is the use of sustained release formulations. Sustained release formulations are designed to slowly release the compound from the tablet or capsule. The slow drug release reduces and prolongs blood levels of drug and thus minimizes the side effects. Sustained release formulations of niacin have been developed, such as Nicobid™ capsules (Rhone-Poulenc Rorer), Endur-acin™ (Innovite Corporation) and U.S. Pat. No. 5,126,145 which describes a sustained release niacin formulation containing two different types of hydroxypropyl methylcellulose and a hydrophobic component.

Studies in hyperlipidemic patients have been conducted with a number of sustained release niacin products. These studies have demonstrated that the sustained release products do not have the same advantageous lipid altering effects as immediate release niacin, and in fact often have a worse side effect profile compared to the immediate release product. The major disadvantage of the sustained release formulations, as can be seen in Knopp et al., 1985, is the significantly lower reduction in triglycerides (−2% for the sustained release versus −38% for the immediate release) and lower increase in HDL cholesterol, represented as $HDL_2$ particles which are known by the art to be most beneficial, (−5% for the sustained release versus +37% for the immediate release).

Additionally, sustained release niacin formulations have been noted as causing greater incidences of liver toxicity as described in Henken et al (Am J Med 91:1991 1991) and Dalton et al (Am J Med 93: 102 1992). There is also great concern regarding the potential of these formulations in disrupting glucose metabolism and uric acid levels.

In a recent edition of the JOURNAL OF THE AMERICAN MEDICAL ASSOCIATION (JAMA), an article appeared which presented research results investigating the liver toxicity problems associated with a sustained release form of nicotinic acid. "A Comparison of the Efficacy and Toxic Effects of Sustained- vs Immediate-Release Niacin in Hypercholesterolemic Patients", McKenney et al., JAMA, Vol. 271, No. 9, Mar. 2, 1994, page 672. The article presented a study of twenty-three patients. Of that number 18 or 78 percent were forced to withdraw because liver function tests (LFTs) increased indicating potential liver damage. The conclusion of the authors of that article was that the sustained release form of niacin "should be restricted from use."

A similar conclusion was reached in an article authored by representatives of the Food and Drug Administration and entitled "Hepatic Toxicity of Unmodified and Time-Release Preparations of Niacin", Rader, et al., THE AMERICAN JOURNAL OF MEDICINE, Vol. 92, January 1992, page 77. Because of these studies and similar conclusions drawn by other heath care professionals, the sustained release forms of niacin have experienced limited utilization.

Therefore, it can be seen from the scientific literature that there is a need for development of a sustained release niacin formulation and a method of delivering said formulation which would provide hyperlipidemic patients with "balanced lipid alteration", i.e. reductions in total cholesterol, LDL cholesterol, triglycerides and Lp(a) as well as increases in HDL cholesterol with an acceptable safety profile, especially as regards liver toxicity and effects on glucose metabolism and uric acid levels.

SUMMARY OF THE INVENTION

It is therefore, an object of the present invention to provide a composition of nicotinic acid or any compound which is metabolized by the body to form nicotinic acid for treating hyperlipidemia.

It is another object of the present invention to provide a composition as above, which has a time release sustaining characteristic.

It is yet another object of the present invention to provide a method for employing a composition as above, for treating hyperlipidemia, which results in little or no liver damage.

At least one or more of the foregoing objects, together with the advantages thereof over the known art relating to the treatment of hyperlipidemia, which shall become apparent from the specification which follows, are accomplished by the invention as hereinafter described and claimed.

In general the present invention provides an improved antihyperlipidemia composition of the oral type employing an effective antihyperlipidemic amount of nicotinic acid, wherein the improvement comprises compounding the nicotinic acid with from about 5% to about 50% parts by weight of hydroxypropyl methylcellulose per hundred parts by weight of tablet or formulation.

The present invention also provides an orally administered antihyperlipidemia composition which comprises from about 30% to about 90% parts by weight of nicotinic acid; and, from about 5% to about 50% parts by weight of hydroxypropyl methylcellulose.

The present invention also includes a method of treating hyperlipidemia in a hyperlipidemic. The method comprises the steps of forming a composition which comprises an effective antihyperlipidemic amount of nicotinic acid and an amount of excipients to provide sustained release of drug. The method also includes the step of orally administering the composition to the hyperlipidemic nocturnally.

A method of treating hyperlipidemia in a hyperlipidemic according to the invention, comprises dosing the hyperlipidemic with an effective antihyperlipidemic amount of nicotinic acid or compound metabolized to nicotinic acid by the body. The dose is given once per day in the evening or at night, combined with a pharmaceutically acceptable carrier to produce a significant reduction in total and LDL cholesterol as well as a significant reduction in triglycerides and Lp(a), with a significant increase in HDL cholesterol.

PREFERRED EMBODIMENTS FOR CARRYING OUT THE INVENTION

The present invention employs nicotinic acid or a compound other than nicotinic acid itself which the body metabolizes into nicotinic acid, thus producing the same effect as described herein. The other compounds specifically include, but are not limited to the following: nicotinyl alcohol tartrate, d-glucitol hexanicotinate, aluminum nicotinate, niceritrol and d,1-alpha-tocopheryl nicotinate. Each such compound will be collectively referred to hereinbelow by "nicotinic acid."

As stated hereinabove, nicotinic acid has been employed in the past for the treatment of hyperlipidemia, which condition is characterized by the presence of excess fats such as cholesterol and triglycerides, in the blood stream. According to the present invention, a sustained release composition of nicotinic acid is prepared as an example. By "sustained release" it is understood to mean a composition which when orally administered to a patient to be treated, the active ingredient will be released for absorption into the blood stream over a period of time. For example, it is preferred that in a dosage of about 1500 milligrams (hereinafter "mgs") of nicotinic acid, approximately 100 percent of the nicotinic acid will be released to the blood stream in about 4 to about 24 hours.

The specific sustained release composition according to the present invention employs an effective antihyperlipidemic amount of nicotinic acid. By "effective antihyperlipidemic amount" it is understood to mean an amount which when orally administered to a patient to be treated, will have a beneficial effect upon the physiology of the patient, to include at least some lowering of total cholesterol, LDL cholesterol, triglycerides and Lp(a) and at least some increase in HDL cholesterol in the patient's blood stream. An exemplary effective antihyperlipidemic amount of nicotinic acid would be from about 250 mgs to about 3000 mgs of nicotinic acid to be administered according to the invention as will be more fully described hereinbelow. This amount will vary dependent upon a number of variables, including the physiological needs of the patient to be treated.

Preferably, there is also included in the sustained release composition according to the present invention, a swelling agent which is compounded with the nicotinic acid, such that when the composition is orally administered to the patient, the swelling agent will swell over time in the patient's gastrointestinal tract, and release the active nicotinic acid, or a compound which produces nicotinic acid into the gastrointestinal system for absorption into the blood stream, over a period of time. As is known in the art, such swelling agents and amounts thereof, may be preselected in order to control the time release of the active ingredient. Such swelling agents include, but are not limited to, polymers such as sodium carboxymethylcellulose and ethylcellulose and waxes such as bees wax and natural materials such as gums and gelatins or mixtures of any of the above. Because the amount of the swelling agent will vary depending upon the nature of the agent, the time release needs of the patient and the like, it is preferred to employ amounts of the agent which will accomplish the objects of the invention.

An exemplary and preferred swelling agent is hydroxypropyl methylcellulose, in an amount ranging from about 5% to about 50% parts by weight per 100 parts by weight of tablet or formulation. The preferred example will ensure a sustained time release over a period of approximately 4–24 hours as demonstrated by in vitro dissolution techniques known to the art.

A binder may also be employed in the present compositions. While any known binding material is useful in the present invention, it is preferred to employ a material such as one or more of a group of polymers having the repeating unit of 1-ethenyl-2-pyrrolidinone. These polymers generally have molecular weights of between about 10,000 and 700,000, and are also known as "povidone".

Amounts of the binder material will of course, vary depending upon the nature of the binder and the amount of other ingredients of the composition. An exemplary amount of povidone in the present compositions would be from about 1% to about 5% by weight of povidone per 100 parts by weight of the total formulation.

Processing aids such as lubricants, including stearic acid, may also be employed, as is known in the art. An exemplary amount of stearic acid in the present compositions would be from about 0.5% to about 2.0% by weight per 100 parts by weight of tablet or formulation.

General Experimental

In order to demonstrate the effectiveness of the compositions and method of the present invention over known antihyperlipidemia compositions and methods heretofore known in the art, a number of substantially identical composition were prepared according to the disclosure hereinabove. The composition ingredients and amounts are listed in TABLE I hereinbelow.

TABLE I

| | Test Tablet Composition | | |
|---|---|---|---|
| Ingredient | 375 mg | 500 mg | 750 mg |
| Nicotinic Acid | 375.0 | 500.0 | 750.0 |
| Hyroxypropyl methylcellulose | 188.7 | 203.0 | 204.7 |

TABLE I-continued

| | Test Tablet Composition | | |
|---|---|---|---|
| Ingredient | 375 mg | 500 mg | 750 mg |
| Povidone | 12.9 | 17.2 | 25.9 |
| Stearic Acid | 5.8 | 7.3 | 9.9 |
| TOTAL | 582.4 mg | 727.5 mg | 990.5 mg |

The ingredients were compounded together to form a tablet. Two study groups consisting of eleven and fourteen patients each were formed. Blood samples were taken from the patients, and tested for total cholesterol, LDL cholesterol, triglycerides and HDL cholesterol to establish baseline levels from which fluctuations in these lipids could be compared. The patients were then placed upon a regimen of the above discussed tablets, totaling approximately 1500 mg of nicotinic acid, once per day before going to bed. After eight weeks of this regimen, the patients were again tested for lipid profiles. The results of the tests conducted at eight weeks, showing the changes in the lipid profiles as a percentage change from the baseline, are reported in the table hereinbelow. Positive numbers reflect percentage increases and negative numbers reflect percentage decreases in this table.

The data reported in TABLE II shows that the LDL levels in the Group A patients had a mean decrease of −13.9% and triglyceride decrease of −18.9%. HDL cholesterol levels, the beneficial cholesterol, were raised by 23.0% in this Group. Similar results were obtained with the Group B patients. These studies demonstrate that dosing the sustained release formulation during the evening hours or at night provides reductions in LDL cholesterol levels equal to immediate release niacin on a milligram per milligram basis, but superior reductions in triglyceride reductions when compared to sustained release formulations dosed during daytime hours on a milligram per milligram basis. Additionally, the increases in HDL cholesterol obtained from dosing the sustained release formulation during the evening or at night were +23.0% for one group and +25.3% for the other group. Dosing during the evening therefore provides reduction in LDL cholesterol plus significant decreases in triglycerides and increases in HDL cholesterol with once-a-day dosing.

Groups A and B were also tested for liver enzymes (AST, ALT and Alkaline Phosphatase), uric acid and fasting glucose levels at the start of the study described hereinabove (to form a baseline) and at two, four and eight week intervals. The results of these tests are listed in TABLES III–VII hereinbelow.

TABLE II

Patient Study Lipid Profile Data

| Pt. No. | Total-C | LDL-C | Apo B | Trigs | HDL-C | $HDL_2$-C | LD(a) |
|---|---|---|---|---|---|---|---|
| GROUP A | | | | | | | |
| 1 | −8.2 | −12.0 | NA | −17.3 | 22.0 | NA | NA |
| 2 | −5.9 | −27.0 | NA | −28.7 | 65.0 | NA | NA |
| 3 | −15.1 | −13.0 | NA | −22.0 | −9.1 | NA | NA |
| 4 | −3.3 | −10.0 | NA | 61.6 | 3.8 | NA | NA |
| 5 | −16.5 | −17.7 | NA | −28.8 | 11.1 | NA | NA |
| 6 | −12.4 | −25.9 | NA | −42.0 | 51.6 | NA | NA |
| 7 | −24.2 | −31.4 | NA | −39.4 | 12.5 | NA | NA |
| 8 | −6.7 | −7.4 | NA | −42.4 | 18.8 | NA | NA |
| 9 | 4.5 | 1.1 | NA | 7.2 | 9.2 | NA | NA |
| 10 | 2.8 | −0.2 | NA | −2.7 | 22.9 | NA | NA |
| 11 | −13.0 | −9.4 | NA | −54.0 | 44.3 | NA | NA |
| Mean | −8.9 | −13.9 | NA | −18.9 | 23.0 | NA | NA |
| p-Value | 0.0004 | 0.0001 | | 0.0371 | 0.0068 | | |
| GROUP B | | | | | | | |
| 1 | −19.2 | −27.1 | −24.4 | −33.4 | 20.0 | 22.3 | −81.9 |
| 2 | −32.2 | −35.7 | −28.0 | −60.4 | 4.3 | 3.2 | −25.3 |
| 3 | −21.4 | −33.6 | −35.6 | −33.4 | 30.4 | 38.6 | −17.4 |
| 4 | −19.9 | −24.6 | −15.1 | −20.8 | 9.6 | 16.1 | −27.0 |
| 5 | −3.3 | −2.1 | −29.4 | −41.1 | 5.8 | 2.4 | −22.4 |
| 6 | | | PATIENT WITHDREW FROM STUDY | | | | |
| 7 | 23.1 | −32.6 | −42.6 | −58.6 | 49.2 | 68.9 | −14.3 |
| 8 | 24.8 | 34.0 | −28.4 | 5.5 | 6.5 | −6.8 | NA |
| 9 | 10.1 | 12.0 | −16.8 | −11.6 | 20.7 | −12.3 | 40.6 |
| 10 | −2.9 | −7.7 | −28.0 | −59.0 | 53.1 | 70.5 | −41.2 |
| 11 | −10.5 | −18.8 | −25.3 | −53.4 | 31.8 | 39.7 | NA |
| 12 | −20.0 | −30.8 | −30.4 | 11.7 | 21.1 | 25.0 | −28.4 |
| 13 | 17.4 | 16.8 | −17.5 | −17.5 | 51.3 | 51.9 | 38.5 |
| 14 | −9.4 | −16.6 | −32.0 | −46.9 | 52.3 | 67.6 | 17.6 |
| Mean | −8.7 | −12.8 | −32.2 | −27.2 | 25.3 | 30.1 | −17.9 |
| p-Value | 0.0002 | <0.0001 | 0.0001 | <0.001 | <0.0001 | 0.0002 | <0.0188 |
| Combined | −8.7 | −13.3 | Gp B | −26.1 | 25.3 | Gp B | Gp B |
| p-Value | 0.0002 | <0.0001 | only | <0.0001 | <0.0001 | only | only |

TABLE III

THE EFFECT OF NIASPAN ™ THERAPY ON AST (SGOT)
LEVELS (U/L)
(1500 mgs dosed once-a-day at night)
(n = 28)

| Pt # | Baseline | 2 Wks. | 4 Wks. | 8 Wks. | Reference Range |
|---|---|---|---|---|---|
| GROUP A | | | | | |
| 1 | 28 | 29 | 25 | 24 | 0–50 |
| 2 | 24 | 25 | 24 | 26 | 0–50 |
| 3 | 17 | 18 | 22 | 21 | 0–50 |
| 4 | 14 | 16 | 15 | 17 | 0–50 |
| 5 | 22 | NA | 32 | 52 | 0–50 |
| 6 | 21 | 17 | 17 | 14 | 0–50 |
| 7 | 17 | 17 | 14 | 18 | 0–50 |
| 8 | 20 | 21 | 22 | 22 | 0–50 |
| 9 | 16 | 16 | 17 | 20 | 0–50 |
| 10 | 18 | 21 | 21 | 25 | 0–50 |
| 11 | 21 | 21 | 22 | 21 | 0–50 |
| GROUP B | | | | | |
| 1 | 23 | 25 | 38 | 33 | 0–50 |
| 2 | 20 | 20 | 21 | 21 | 0–50 |
| 3 | 15 | 20 | 18 | 19 | 0–50 |
| 4 | 25 | 22 | 25 | 26 | 0–50 |
| 5 | 23 | 21 | 17 | 18 | 0–50 |
| 6 | PATIENT WITHDREW DUE TO FLUSHING | | | | |
| 7 | 21 | 18 | 18 | 19 | 0–50 |
| 8 | 18 | 19 | 18 | 19 | 0–50 |
| 9 | 15 | 16 | 18 | 15 | 0–50 |
| 10 | 16 | 15 | 19 | 28 | 0–50 |
| 11 | 20 | 22 | 24 | 28 | 0–50 |
| 12 | 23 | 25 | 28 | 22 | 0–50 |
| 13 | 20 | 15 | 20 | 19 | 0–50 |
| 14 | 18 | 25 | 20 | 18 | 0–50 |
| Combined Mean | 19.8 | 20.4 | 20.8 | 21.1 | |
| Change From Baseline | | +3.0% | +5.1% | +6.6% | |

Level of Significance: p = 0.4141

TABLE IV

THE EFFECT OF NIASPAN ™ THERAPY ON ALT (SGPT)
LEVELS (U/L)
(1500 mgs dosed once-a-day at night)
(n = 28)

| Pt # | Baseline | 2 Wks. | 4 Wks. | 8 Wks. | Reference Range |
|---|---|---|---|---|---|
| GROUP A | | | | | |
| 1 | 32 | 28 | 39 | 30 | 0–55 |
| 2 | 24 | 25 | 23 | 26 | 0–55 |
| 3 | 18 | 23 | 30 | 30 | 0–55 |
| 4 | 7 | 13 | 14 | 14 | 0–55 |
| 5 | 14 | NA | 43 | 46 | 0–55 |
| 6 | 22 | 11 | 14 | 10 | 0–55 |
| 7 | 9 | 7 | 11 | 7 | 0–55 |
| 8 | 16 | 18 | 23 | 21 | 0–55 |
| 9 | 14 | 17 | 20 | 14 | 0–55 |
| 10 | 14 | 15 | 17 | 19 | 0–55 |
| 11 | 18 | 18 | 20 | 16 | 0–55 |
| GROUP B | | | | | |
| 1 | 16 | 17 | 27 | 29 | 0–55 |
| 2 | 16 | 14 | 15 | 22 | 0–55 |
| 3 | 13 | 21 | 13 | 16 | 0–55 |
| 4 | 23 | 20 | 26 | 17 | 0–55 |
| 5 | 21 | 23 | 17 | 15 | 0–55 |
| 6 | PATIENT WITHDREW DUE TO FLUSHING | | | | |
| 7 | 21 | 16 | 18 | 21 | 0–55 |
| 8 | 18 | 20 | 17 | 18 | 0–55 |
| 9 | 11 | 5 | 11 | 8 | 0–55 |
| 10 | 8 | 10 | 14 | 17 | 0–55 |
| 11 | 17 | 12 | 18 | 16 | 0–55 |
| 12 | 14 | 18 | 20 | 16 | 0–55 |
| 13 | 14 | NA | 11 | 10 | 0–55 |
| 14 | 23 | 23 | 19 | 19 | 0–55 |
| Combined Mean | 17.7 | 17.5 | 19.3 | 18.2 | |
| Change From Baseline | | −1.1% | 9.0% | +2.8% | |

Level of Significance: p = 0.3424

TABLE V

THE EFFECT OF NIASPAN ™ THERAPY
ON ALKALINE PHOSPHATASE LEVELS (U/L)
(1500 mgs dosed once-a-day at night)
(n = 28)

| Pt # | Baseline | 2 Wks. | 4 Wks. | 8 Wks. | Reference Range |
|---|---|---|---|---|---|
| GROUP A | | | | | |
| 1 | 52 | 56 | 57 | 55 | 20–140 |
| 2 | 103 | 100 | 89 | 102 | 20–140 |
| 3 | 54 | 45 | 53 | 51 | 20–140 |
| 4 | 70 | 68 | 71 | 91 | 20–140 |
| 5 | 77 | NA | 74 | 81 | 20–140 |
| 6 | 55 | 48 | 49 | 51 | 20–140 |
| 7 | 72 | 71 | 79 | 75 | 20–140 |
| 8 | 55 | 49 | 47 | 50 | 20–140 |
| 9 | 53 | 55 | 56 | 45 | 20–140 |
| 10 | 74 | 73 | 75 | 75 | 20–140 |
| 11 | 18 | 18 | 20 | 16 | 20–140 |
| GROUP B | | | | | |
| 1 | 73 | 67 | 89 | 95 | 20–140 |
| 2 | 82 | 64 | 72 | 71 | 20–140 |
| 3 | 73 | 69 | 72 | 82 | 20–140 |
| 4 | 37 | 36 | 37 | 38 | 20–140 |
| 5 | 65 | 53 | 54 | 61 | 20–140 |
| 6 | PATIENT WITHDREW DUE TO FLUSHING | | | | |
| 7 | 64 | 58 | 58 | 58 | 20–140 |
| 8 | 79 | 78 | 65 | 73 | 20–140 |
| 9 | 94 | 92 | 103 | 93 | 20–140 |
| 10 | 69 | 67 | 70 | 65 | 20–140 |
| 11 | 59 | 67 | 63 | 72 | 20–140 |
| 12 | 65 | 59 | 59 | 63 | 20–140 |

TABLE V-continued

THE EFFECT OF NIASPAN ™ THERAPY
ON ALKALINE PHOSPHATASE LEVELS (U/L)
(1500 mgs dosed once-a-day at night)
(n = 28)

| | | Weeks Of Therapy With NIASPAN ™ | | | Reference |
|---|---|---|---|---|---|
| Pt # | Baseline | 2 Wks. | 4 Wks. | 8 Wks. | Range |
| 13 | 64 | 68 | 66 | 64 | 20–140 |
| 14 | 72 | 61 | 59 | 64 | 20–140 |
| Combined Mean | 65.5 | 61.5 | 63.3 | 65.8 | |
| Change From Baseline | | −6.1% | −3.4% | +0.005% | |

Level of Significance: p = 0.0236

TABLE VI

THE EFFECT OF NIASPAN ™ THERAPY
ON URIC ACID LEVELS (mg/dL)
(1500 mgs dosed once-a-day at night)
(n = 28)

| | | Weeks Of Therapy With NIASPAN ™ | | | Reference |
|---|---|---|---|---|---|
| Pt # | Baseline | 2 Wks. | 4 Wks. | 8 Wks. | Range |
| GROUP A | | | | | |
| 1 | 5.2 | 5.0 | 4.8 | 4.3 | 4.0–8.5 |
| 2 | 4.0 | 4.6 | 4.5 | 6.2 | 2.5–7.5 |
| 3 | 6.3 | 7.0 | 6.5 | 6.2 | 4.0–8.5 |
| 4 | 3.1 | 4.6 | 4.2 | 3.8 | 2.5–7.5 |
| 5 | 3.4 | NA | 3.3 | 4.2 | 2.5–7.5 |
| 6 | 6.6 | 5.5 | 5.6 | 4.7 | 4.0–8.5 |
| 7 | 3.8 | 4.5 | 4.3 | 4.9 | 2.5–7.5 |
| 8 | 4.4 | 3.8 | 5.1 | 4.5 | 2.5–7.5 |
| 9 | 3.9 | 4.5 | 4.6 | 3.5 | 2.5–7.5 |
| 10 | 2.6 | 2.9 | 2.8 | 2.7 | 2.5–7.5 |
| 11 | 4.7 | 5.5 | 5.2 | 5.3 | 2.5–7.5 |
| GROUP B | | | | | |
| 1 | 3.7 | 4.2 | 4.7 | 3.5 | 2.5–7.5 |
| 2 | 2.8 | 3.5 | 3.6 | 2.3 | 4.0–8.5 |
| 3 | 4.2 | 5.3 | 5.5 | 5.3 | 2.5–7.5 |
| 4 | 4.7 | 3.9 | 5.1 | 3.6 | 4.0–8.5 |
| 5 | 3.7 | 4.1 | 4.1 | 3.8 | 2.5–7.5 |
| 6 | PATIENT WITHDREW DUE TO FLUSHING | | | | |
| 7 | 5.8 | 6.6 | 6.6 | 6.8 | 2.5–7.5 |
| 8 | 4.7 | 4.3 | 5.4 | 5.6 | 2.5–7.5 |
| 9 | 3.7 | 4.6 | 5.1 | 3.8 | 2.5–7.5 |
| 10 | 4.2 | 5.0 | 4.4 | 8.5 | 2.5–7.5 |
| 11 | 1.9 | 3.0 | 2.8 | 5.0 | 2.5–7.5 |
| 12 | 5.6 | 5.4 | 6.2 | 5.6 | 4.0–8.5 |
| 13 | 4.2 | 4.6 | 4.6 | 5.3 | 2.5–7.5 |
| 14 | 5.5 | 5.4 | 6.1 | 5.3 | 2.5–7.5 |
| Combined Mean | 4.54 | 4.82 | 4.92 | 4.86 | *p = 0.3450 |
| Change From Baseline | | +6.2% | +8.4% | +7.0% | |

*Level of Significance: p = 0.3450

TABLE VII

THE EFFECT OF NIASPAN ™ THERAPY
ON FASTING GLUCOSE LEVELS (mg/dL)
(1500 mgs dosed once-a-day at night)
(n = 28)

| | | Weeks Of Therapy With NIASPAN ™ | | | Reference |
|---|---|---|---|---|---|
| Pt # | Baseline | 2 Wks. | 4 Wks. | 8 Wks. | Range |
| GROUP A | | | | | |
| 1 | 114 | 122 | 123 | 110 | 70–115 |
| 2 | 101 | 105 | 107 | 101 | 80–125 |
| 3 | 99 | 98 | 109 | 103 | 70–115 |
| 4 | 100 | 118 | 94 | 94 | 80–125 |
| 5 | 89 | NA | 82 | 103 | 80–125 |
| 6 | 97 | 103 | 94 | 107 | 70–115 |
| 7 | 85 | 107 | 100 | 94 | 80–125 |
| 8 | 98 | 107 | 103 | 101 | 80–125 |
| 9 | 97 | 97 | 100 | 110 | 80–125 |
| 10 | 94 | 101 | 111 | 97 | 70–115 |
| 11 | 102 | 103 | 95 | 95 | 80–125 |
| GROUP B | | | | | |
| 1 | 101 | 97 | 83 | 99 | 70–115 |
| 2 | 90 | 95 | 96 | 89 | 80–125 |
| 3 | 96 | 98 | 95 | 97 | 70–115 |
| 4 | 116 | 139 | 113 | 125 | 80–125 |
| 5 | 88 | 92 | 91 | 95 | 70–115 |
| 6 | PATIENT WITHDREW DUE TO FLUSHING | | | | |
| 7 | 106 | 114 | 118 | 117 | 70–115 |
| 8 | 95 | 106 | 106 | 108 | 70–115 |
| 9 | 81 | 92 | 84 | 92 | 70–115 |
| 10 | 108 | 117 | 122 | 105 | 70–115 |
| 11 | 85 | 106 | 106 | 108 | 70–115 |
| 12 | 92 | 89 | 101 | 86 | 80–125 |
| 13 | 99 | 105 | 94 | 100 | 70–125 |
| 14 | 100 | 108 | 84 | 107 | 70–125 |
| Combined Mean | 98.4 | 105.8 | 101.6 | 102.3 | |
| Change From Baseline | | +7.5% | +3.3% | +4.0% | |

Level of Significance: p = 0.0021

In order to provide a comparison between the state of the art prior to the present invention, and in order to quantify the magnitude of the improvement that the invention provides over the prior art, another study was conducted. This study included 240 patients dosed according to the present invention as described hereinabove. Compared to this group was the group of patients studied by McKenney et al., as reported hereinabove. The results of this study are reported in TABLE VIII hereinbelow.

TABLE VIII

A Comparison of Changes in Liver Function Tests

| | DOSE | | | | | | | |
|---|---|---|---|---|---|---|---|---|
| | 0 | 500 | 1000 | 1500 | 2000 | 2500 | 3000 | TOTAL |
| McKenney SR[b] Niacin[a] | | | | | | | | |
| AST | 23.8 | 27.9 | 40.4 | 36.6 | 56.5 | na | 97.0 | |
| % | − | 117 | 170 | 154 | 237 | na | 408 | |
| Invention Dosage[c] | | | | | | | | |
| AST | 24.3 | na | 23.7 | 27.5 | 26.6 | 27.6 | 27.8 | |
| % | − | na | 98 | 113 | 109 | 114 | 114 | |

TABLE VIII-continued

A Comparison of Changes in Liver Function Tests

| | DOSE | | | | | | | |
|---|---|---|---|---|---|---|---|---|
| | 0 | 500 | 1000 | 1500 | 2000 | 2500 | 3000 | TOTAL |
| McKenney SR Niacin | | | | | | | | |
| ALT | 25.6 | 29.5 | 36.3 | 39.0 | 59.1 | na | 100.0 | |
| % | – | 115 | 142 | 152 | 231 | na | 391 | |
| Invention Dosage | | | | | | | | |
| ALT | 21.4 | na | 18.7 | 22.6 | 21.3 | 22.4 | 21.8 | |
| % | – | na | 87 | 106 | 100 | 105 | 102 | |
| McKenney SR Niacin | | | | | | | | |
| ALK | 95 | 95 | 106 | 105 | 136 | na | 135 | |
| % | – | 100 | 112 | 111 | 143 | na | 142 | |
| Invention Dosage | | | | | | | | |
| ALK | 74.7 | na | 73.9 | 76.1 | 73.4 | 76.7 | 78.0 | |
| % | – | na | 99 | 102 | 98 | 103 | 104 | |
| McKenney SR Niacin | | | | | | | | |
| Drop | – | 0 | 2 | 2 | 7 | na | 7 | 18 |
| n | – | – | – | – | – | – | – | 23 |
| % | – | 0 | 9 | 9 | 30 | na | 30 | 78 |
| Invention Dosage | | | | | | | | |
| Drop | – | – | 0 | 0 | 0 | 0 | 0 | 0 |
| n | – | – | 26 | 67 | 97 | 35 | 15 | 240 |
| % | – | – | 0 | 0 | 0 | 0 | 0 | 0 |
| 1 year | – | – | 15 | 46 | 77 | 31 | 15 | 184 |
| 1 year | – | – | 58 | 69 | 79 | 89 | 100 | 77 |

[a]Dosed twice-per-day as described in "A Comparison of the Efficacy and Toxic Effects of Sustained-vs Immediate-Release Niacin in Hypercholesterolemic Patients" by McKenney et al. Journal of the American Medical Association, March 2, 1994; Vol. 271, No. 9, pages 672–677.
[b]SR is "sustained release"
[c]Dosed once-per-day at night The results of the comparison of the studies reported in TABLE VIII show that the control group (the McKenney group) had 18 of 23, or 78 percent of the patients therein drop out of the test because of an increase in their respective liver function tests. The patients withdrew at the direction of the investigator. In comparison, a group of 240 patients treated according to the present invention had zero patients drop out, based upon the same criteria for withdrawal. The tests results reported above indicate that this sustained release dosage form caused no elevation in liver function tests (i.e., no liver damage), no elevations in uric acid and only a small, 7.5% increase in fasting glucose levels which in fact decreased during continued therapy.

Thus it should be evident that the compositions and method of the present invention are highly effective in controlling hyperlipidemia in hyperlipidemics, by reducing the levels of LDL cholesterol, triglyceride and Lp(a) while increasing HDL cholesterol levels. The present invention is also demonstrated not to cause elevations in liver function tests, uric acid or glucose levels for the hyperlipidemics.

Based upon the foregoing disclosure, it should now be apparent that the use of the compositions and methods described herein will carry out the objects set forth hereinabove. It is, therefore, to be understood that any variations in sustained release formulation evident fall within the scope of the claimed invention and thus, the selection of specific component elements can be determined without departing from the spirit of the invention herein disclosed and described. In particular, sustained release excipients, binders and processing aids according to the present invention are not necessarily limited to those exemplified hereinabove. Thus, the scope of the invention shall include all modifications and variations that my fall within the scope of the attached claims.

What is claimed is:

1. A method of treating hyperlipidemia in a hyperlipidemic comprising dosing the hyperlipidemic with an effective antihyperlipidemic amount of nicotinic acid once per day in the evening or at night, wherein said nicotinic acid is combined with at least one pharmaceutically acceptable carrier to form an oral solid dosage form.

2. A method, as set forth in claim 1, wherein the hyperlipidemic is dosed with from about 250 milligrams to about 3000 milligrams of nicotinic acid.

3. A method as set forth in claim 1 which causes little or no serious liver damage.

4. A method as set forth in claim 1 wherein the release rate of said nicotinic acid is from about 2.0% per hour to about 25% per hour.

5. A method as set forth in claim 1 wherein said nicotinic acid is prepared by formulating the active compound with from about 5 to about 50 parts by weight of hydroxypropyl methylcellulose per 100 parts by weight of tablet.

6. A method, as set forth in claim 1, wherein said nicotinic acid is dosed in the form of a sustained release tablet containing from about 1 to about 4 parts by weight of binder per 100 parts by weight of tablet.

7. A method, as set forth in claim 6, wherein said binder is polyvinyl pyrrolidone.

8. A method, as set forth in claim 1, wherein said nicotinic acid is dosed in the form of a sustained release tablet comprising from about 0.5 to about 2.5 parts by weight of a lubricating agent per 100 parts by weight of tablet.

9. A method, as set forth in claim 8, wherein said lubricating agent is selected from the group consisting of stearic acid and magnesium stearate.

10. A method of treating hyperlipidemia in a hyperlipidemic comprising the administration of an effective antihyperlipidemic amount of a nicotinic acid composition once per day in the evening or at night, wherein said nicotinic acid composition is an oral solid dosage form that consists essentially of nicotinic acid, hydroxypropyl methylcellulose, a water-soluble binder and a lubricant.

11. A method of claim 10, wherein the water-soluble binder is povidone.

12. A method of claim 10, wherein the lubricant is stearic acid.

13. A method of claim 10, wherein the water-soluble binder is povidone and the lubricant is stearic acid.

* * * * *

UNITED STATES PATENT AND TRADEMARK OFFICE
CERTIFICATE OF CORRECTION

PATENT NO. : 6,080,428
APPLICATION NO. : 08/368378
DATED : June 27, 2000
INVENTOR(S) : David J. Bova It is certified that error appears in the above-identified patent and that said Letters Patent is hereby corrected as shown below:

At column 2, line 28, please delete the phrase "18 or 78 percent" and insert the phrase --12 or 52 percent --.

At column 11, line 46, please delete the phrase "had 18 of 23, or 78 percent" and insert the phrase --had 12 of 23, or 52 percent--.

UNITED STATES PATENT AND TRADEMARK OFFICE
CERTIFICATE OF CORRECTION

| | |
|---|---|
| PATENT NO. | : 6,080,428 |
| APPLICATION NO. | : 08/368378 |
| DATED | : June 27, 2000 |
| INVENTOR(S) | : David J. Bova |

It is certified that error appears in the above-identified patent and that said Letters Patent is hereby corrected as shown below:

At column 10, line 51 to column 11, line 43, please replace Table VIII with the following replacement table:

TABLE VIII
A Comparison of Changes in Liver Function Tests

| | DOSE | | | | | | | |
|---|---|---|---|---|---|---|---|---|
| | 0 | 500 | 1000 | 1500 | 2000 | 2500 | 3000 | TOTAL |
| McKenney SR[b]Niacin | | | | | | | | |
| AST | 23.8 | 27.9 | 40.4 | 36.6 | 56.5 | na | 97.0 | |
| % | -- | 117 | 170 | 154 | 237 | na | 408 | |
| Invention Dosage[c] | | | | | | | | |
| AST | 24.3 | na | 23.7 | 27.5 | 26.6 | 27.6 | 27.8 | |
| % | -- | na | 98 | 113 | 109 | 114 | 114 | |
| McKenney SR Niacin | | | | | | | | |
| AST | 25.6 | 29.5 | 36.3 | 39.0 | 59.1 | na | 100.0 | |
| % | -- | 115 | 142 | 152 | 231 | na | 391 | |
| Invention Dosage | | | | | | | | |
| ALT | 21.4 | na | 18.7 | 22.6 | 21.3 | 22.4 | 21.8 | |
| % | -- | na | 87 | 106 | 100 | 105 | 102 | |
| McKenney SR Niacin | | | | | | | | |
| ALK | 95 | 95 | 106 | 105 | 136 | na | 135 | |
| % | -- | 100 | 112 | 111 | 143 | na | 142 | |
| Invention Dosage | | | | | | | | |
| ALK | 74.7 | na | 73.9 | 76.1 | 73.4 | 76.7 | 78.0 | |
| % | -- | na | 99 | 102 | 98 | 103 | 104 | |
| McKenney SR Niacin | | | | | | | | |
| Drop | -- | 0 | 1 | 2 | 4 | na | 5 | 12 |
| n | -- | -- | -- | -- | -- | -- | -- | 23 |
| % | -- | 0 | 4 | 9 | 17 | na | 22 | 52 |
| Invention Dosage | | | | | | | | |
| Drop | -- | -- | 0 | 0 | 0 | 0 | 0 | 0 |
| n | -- | -- | 26 | 67 | 97 | 35 | 15 | 240 |
| % | -- | -- | 0 | 0 | 0 | 0 | 0 | 0 |
| 1 year | -- | -- | 15 | 47 | 77 | 31 | 15 | 184 |
| 1 year | -- | -- | 58 | 69 | 79 | 89 | 100 | 77 |

Dosed twice-per-day as described in "A Comparison of the Efficacy and Toxic Effects of Sustained - vs. Immediate - Release Niacin in Hypercholesterolemic Patients" by McKenney et al., *Journal of the American Medical Association*, March 2, 1994; Vol. 271, No. 9, pages 672-677.
[b] SR is "sustained release"
[c] Dosed once-per-day at night Signed and Sealed this Nineteenth Day of December, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,080,428 | Page 1 of 1 |
| APPLICATION NO. | : 08/368378 | |
| DATED | : June 27, 2000 | |
| INVENTOR(S) | : David J. Bova | |

It is certified that error appears in the above-identified patent and that said Letters Patent is hereby corrected as shown below:

On the cover page, under [22] Filed:, change "Jan. 14, 1995" to --Jan. 4, 1995--

Signed and Sealed this
Eighth Day of February, 2011

David J. Kappos
*Director of the United States Patent and Trademark Office*